United States Patent [19]

Neuelmann et al.

[11] Patent Number: 4,683,419

[45] Date of Patent: Jul. 28, 1987

[54] METHOD AND APPARATUS FOR DETECTING FAULTS IN A STRUCTURE BY MEASURING VOLTAGE DROP BETWEEN SURFACE POINTS THEREOF

[75] Inventors: Rolf Neuelmann, Bergisch-Gladbach; Manfred Fortmann, Overath, both of Fed. Rep. of Germany

[73] Assignee: Interatom GmbH, Bergisch-Gladbach, Fed. Rep. of Germany

[21] Appl. No.: 778,548

[22] Filed: Sep. 20, 1985

[30] Foreign Application Priority Data

Sep. 21, 1984 [DE] Fed. Rep. of Germany ....... 3434801
Jan. 18, 1985 [DE] Fed. Rep. of Germany ....... 3501614

[51] Int. Cl.⁴ .................... G01R 27/14; G01R 27/26; G01N 27/82
[52] U.S. Cl. ...................................... 324/64; 324/263
[58] Field of Search ................ 324/57 R, 64, 263

[56] References Cited

U.S. PATENT DOCUMENTS

| | | | |
|---|---|---|---|
| 2,351,201 | 6/1944 | Gillis | 324/64 |
| 3,281,681 | 10/1966 | Stevenson | 324/64 X |
| 3,665,302 | 5/1972 | Lees et al. | 324/64 |
| 3,753,089 | 8/1973 | Gunn et al. | 324/133 X |
| 4,048,558 | 9/1977 | Goodman | 324/57 R |
| 4,266,185 | 5/1981 | Charlesworth et al. | 324/64 |

FOREIGN PATENT DOCUMENTS 2228277 12/1973 Fed. Rep. of Germany .
8303675 10/1983 PCT Int'l Appl. .

Primary Examiner—Gerard R. Strecker
Attorney, Agent, or Firm—Herbert L. Lerner; Laurence A. Greenberg

[57] ABSTRACT

A method for monitoring structures by measuring electrical quantities including subjecting an electrically conducting component to an a-c current with a predetermined frequency in a given direction generating a magnetic flux in a given direction, tapping a voltage drop across two measurement points mutually spaced apart by a given distance at individual partial regions of the component with two measuring lines contacting the component, forming a first conductor loop from the measuring lines and the component with an inductively effective area being as small as possible, forming a second conductor loop being substantially parallel to the given direction of the current and perpendicular to the given direction of the magnetic flux, tapping an induction voltage from the change of the magnetic flux as close as possible to the measurement points with the second conductor loop, feeding the voltage drop and the induction voltage to an electronic evaluation circuit, and deriving the local resistance of the component at the measurement points from the voltage drop and the induction voltage with the evaluation circuit and an apparatus for carrying out the method.

24 Claims, 6 Drawing Figures

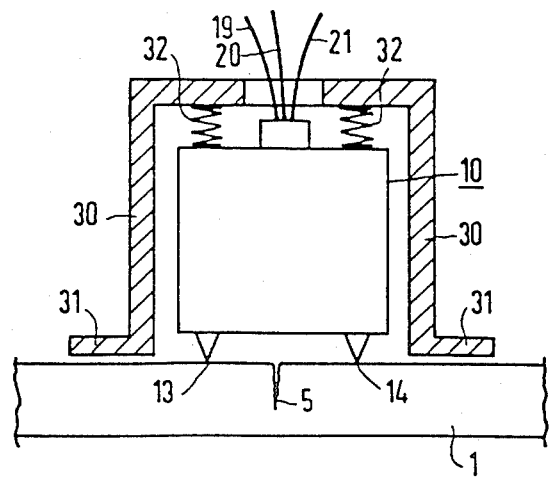
FIG 3
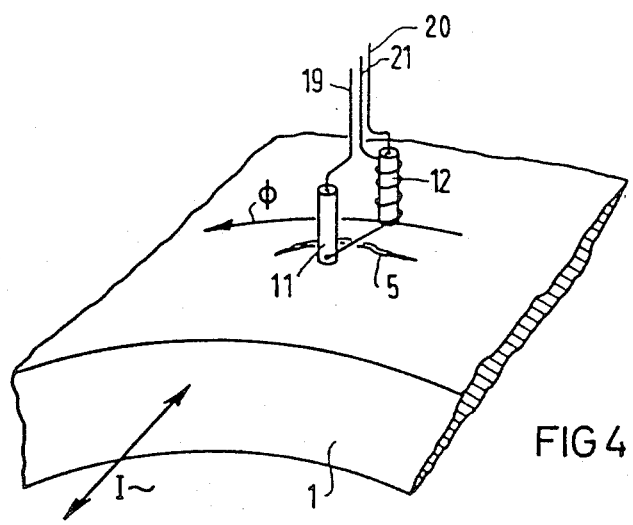
FIG 4
FIRST LOOP:
21-16b-16a-15-
-13-(5-50)-14-12-
-18-20
FIG 5a
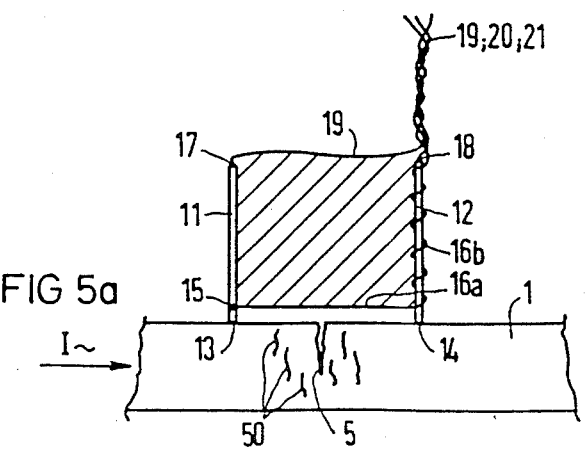

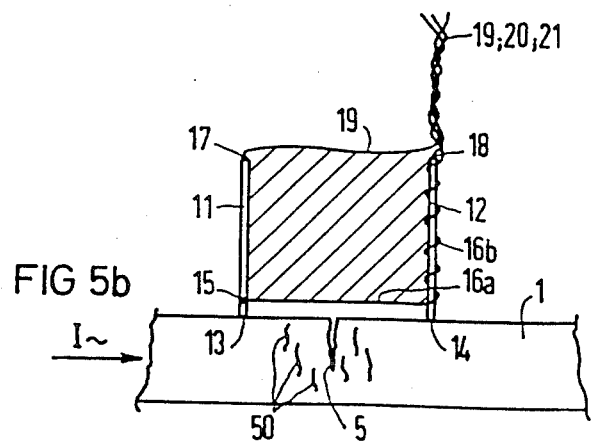

METHOD AND APPARATUS FOR DETECTING FAULTS IN A STRUCTURE BY MEASURING VOLTAGE DROP BETWEEN SURFACE POINTS THEREOF

The invention relates to a method for monitoring structures by measuring electrical quantities where, for instance, an electrically conducting component is acted upon by an a-c current of predeterminable frequency and the voltage drop across individual partial regions is measured.

The invention also relates to an apparatus for carrying out the method, including an a-c current source for acting upon a component with an a-c current, as well as an electronic evaluation circuit in which the voltages taken off at the component can be processed. In monitoring components of electrically conductive materials, for instance, electrical properties are also measured, among other things. For example, the electrical resistance of a material is changed if cracks or other inhomogeneities are formed therein. This information may be utilized in the eddy current testing of components.

The prior art methods for monitoring structures by measuring electrical quantities are not suitable for all applications and often cannot be carried out with sufficient accuracy. Especially in the case of monitoring or periodic examination of highly stressed structures for fatigue phenomena such as micro cracks, the prior art provides no precise yet simple measuring methods for the electrical properties.

Although a method for monitoring components by measuring electric voltages is already known from International Publication No. WO 83/03675, the reproducibility and accuracy of the measurements are insufficient for some applications.

It is accordingly an object of the invention to provide a method for monitoring structures by measuring electrical quantities, which overcomes the hereinafore-mentioned disadvantages of the heretofore-known methods of this general type and which achieves especially high precision and validity of measurements. On one hand, the method should also be suitable especially for the continuous examination of hot structures. However, on the other hand it should permit mobile use. It is also an object of the invention to provide an apparatus and a corresponding measuring head for carrying out the method, which overcomes the above-mentioned disadvantages.

With the foregoing and other objects in view there is provided, in accordance with the invention, a method for monitoring structures by measuring electrical quantities, which comprises subjecting an electrically conducting component to an a-c current with a predetermined frequency in a given direction generating a magnetic flux in a given direction, tapping a voltage drop across two measurement points mutually spaced apart by a given distance at individual partial regions of the component with two measuring lines contacting the component, forming a first conductor loop from the measuring lines and the component with an inductively effective area being as small as possible, forming a second conductor loop being substantially parallel to the given direction of the current and perpendicular to the given direction of the magnetic flux, tapping off or measuring an induction voltage from the change of the magnetic flux as close as possible to the measuring points with the second conductor loop, feeding the voltage drop and the induction voltage to an electronic evaluation circuit for measuring the voltage drop, and deriving the local resistance of the component at the measurement points from the voltage drop and the induction voltage with the evaluation circuit.

In accordance with another mode of the invention, there is provided a method which comprises preamplifying the voltage drop and the induction voltage before feeding them to the evaluation circuit.

In accordance with an additional mode of the invention, there is provided a method which comprises considering the phase relationships of the voltage drop and the induction voltage relative to each other or to the a-c current when deriving the local resistance with the evaluation circuit.

In accordance with an added mode of the invention, there is provided a method which comprises deriving quantities significant for determining the condition of the component with the evaluation circuit, besides deriving the local resistance.

If a component is acted upon by an electric a-c current, this current flows mainly in a region close to the outer surface of the structure, as a function of the frequency. If the surface of the structure contains inhomogeneities in some regions, this results in an increased electric resistance, so that a higher voltage drop per unit length occurs than in undamaged regions. For a precise measurement of the electric resistance between two measuring points, the voltage drop there must be measured as accurately as possible. Two problems have arisen to date with such measurements. On one hand, the a-c current flowing in the structure generates a magnetic a-c field which circulates around the structure and can generate an interference voltage in the measuring lines. In order to prevent this, it is proposed that the measuring lines through which the voltage between two measuring points is tapped off, be installed as close together as possible and be twisted around each other so that a conductor loop with only a very small inductively effective area is formed. In this manner, interference by magnetic fields can be reduced to negligible values. On the other hand, the current distribution in the component and the phase of the a-c current are not always sufficiently constant and known. This has been found to be a problem, especially at higher frequencies, since changes in the frequency, the magnitude of the current and even the position of the electric leads running to the structure would change the phase relationships. As a remedy, the method of the invention described above provides for the change of the magnetic flux generated by the a-c current to be measured as closely as possible to the measuring points as an induction i.e. "induced" voltage, by means of a conductor loop. Except for a phase shift of 90°, this induction voltage corresponds exactly to the a-c current flowing at the measuring point. Highly reproducible measurements can be made with this method according to the invention, since the voltage as well as the current including their phases at the measuring point are now known, and the local resistance, for instance, can be determined therefrom.

In accordance with a further mode of the invention, there is provided a method which comprises sequentially or simultaneously measuring the electrical quantities under the same conditions with identical measuring apparatus at a region to be examined at an unstressed and undamaged reference measuring point. Measuring at a reference measuring point having properties which are known exactly and measuring at a point to be examined in comparison thereto, permits most systematic errors to be eliminated. Only the ratio of the individual measurement results to the reference measurements is important.

In accordance with again an additional mode of the invention, there is provided a method which comprises measuring and keeping constant the phase relationships between the a-c current and the tapped off or "measured" voltage drop and induction i.e. "induced" voltage with a frequency and phase selective lock-in amplifier in the evaluation circuit. This measuring method is particularly advantageous for very small a-c voltages containing interferences. The lock-in amplifier can cause the tapped-off voltages to be selected and amplified only with very definite phase relationships relative to each other or to the a-c current in the component. Data significant for determining the state of the component can be derived from the absolute values of the tapped-off voltages and/or the phases.

In accordance with again an added mode of the invention, there is provided a method which comprises automatically readjusting the phase at the lock-in amplifier with each measurement for measuring the prevailing voltage drop with a phase shift that is always exactly 90° relative to the corresponding induction voltage. This simplifies the measuring operation and permits the automatic sequential sampling of many measuring points with a lock-in amplifier, for instance, with the aid of a conventional digital multiplexer.

In accordance with again a further mode of the invention, there is provided a method which comprises accurately measuring the induction voltage and forming a ratio of the induction voltage to the phase-shifted voltage drop as a measure of damage to and change in the component. The voltage induced in the conductor loop by the magnetic a-c field is proportional to the a-c current flowing at the measuring point, except for the phase shift. This means that with the method according to the invention, the current and the voltage at the measuring point can be measured, except for a proportionality factor, depending on the measuring setup. The resistance of the material at the measuring point can be calculated from this, according to Ohm's law, if the proportionality factor is known. In order to determine this respective resistivity in the region to be examined, neither a reference measurement nor the exact knowledge of the current distribution in the structure is required, since the necessary measurement values can be obtained locally. This increases the precision and reproducibility of the measurement quite considerably. Further details will be explained by making reference to the drawings.

With the objects of the invention in view, there is furthermore provided an apparatus for monitoring structures by measuring electrical quantities, comprising a measuring device including an a-c current source connected to a component for subjecting the component to an a-c current in a given direction generating a magnetic flux in a given direction, measuring lines contacting measurement points on the surface of the component for tapping a voltage drop, other electrically conducting parts connected to the measuring lines, the measuring lines, the other electrically conducting parts and the component together forming a first conductor loop with an inductively effective area being as small as possible, a second conductor loop substantially parallel to the given direction of the a-c current and perpendicular to the given direction of the magnetic flux for measuring the change of the magnetic flux as an induction voltage, the second conductor loop being as close as possible to the measurement points and to the surface of the component, and an electronic evaluation circuit connected to the measuring lines including means for simultaneously, quasisimultaneously or alternatingly measuring the induction voltage and processing the voltage drop.

In accordance with still another feature of the invention, the evaluation circuit includes means for measuring the induction voltage while considering the phase relationship of the voltage drop and the induction voltage relative to each other or to the a-c current. It is essential that the measuring lines which tap off the voltage drop at the measuring point form a loop with an inductively effective area that is as small as possible, so that interference is eliminated. In addition, the device must have a supplemental conductor loop for measuring the changes of the magnetic flux.

In accordance with still an added feature of the invention, the measuring device is attached to a location of the component with known properties, and including at least one other measuring device identical to the first-mentioned measuring device being attached to at least one location of the component to be examined. This is done for reference purposes.

In accordance with still an additional feature of the invention there is provided a measuring head having first and second pins electrically conductingly contacting the measurement points of the component, the first and second pins having upper ends and the second pin having a tap, the measuring lines being in the form of a first measuring line connected to the upper end of the first pin and a second measuring line having an upper region twisted with the first measuring line up to the upper end of the first pin and another region ending at the tap of the second pin, and including a lead fastened to the upper end of the second pin and twisted with the measuring lines, the measuring head additionally including the second conductor loop including the second pin, the lead twisted with the measuring lines and the second measuring line.

In accordance with still a further feature of the invention, the other region of the second measuring line is wound around the first pin or adjacent or close to the first pin or adjacent the surface of the component.

In accordance with yet another feature of the invention, the measuring head is a compact unit cast over with electrically insulating material such as water glass.

In accordance with yet an additional feature of the invention, the measuring head is a mobile probe and the pins have hardened points at lower ends thereof to be pressed against the component.

In accordance with yet an added feature of the invention, there is provided a holding frame for the measuring head having support elements defining a contact surface for the component and means such as compression springs or elastic parts for biasing the top of the measuring head against the component, the pins protruding beyond the contact surface in a relaxed or load-relieved condition of the biasing means.

In accordance with yet a further feature of the invention, the measuring head, the measuring lines and the lead twisted thereto form a prefabricated unit disposed on and connected to the pins preferably by screws with electrical contact.

In accordance with a concomitant feature of the invention, there is provided a preamplifier integrated in the measuring head.

This provides a particularly ruggedly constructed measuring head for carrying out the method, as explained in greater detail with reference to the drawings and with the aid of an embodiment example. Measuring heads according to the invention can be constructed either as mobile probes or as fixed instrumentation for the continuous monitoring of a component, which may be welded on. Since a permanently mounted probe must follow elongations of the component without causing damage, the probe should be cast into a suitable material. Different materials are available for this purpose, depending on the temperature range of the application, with which a person skilled in the art is familiar. Prefabricated units which are screwed to welded-on measuring pins in a simple manner are also possible.

Depending on the desired properties, the probe can be built in such a way that the additional conductor loop follows or does not follow elongations of the component, i.e. by providing changes of the spacing of the measuring points manifested as an enlargement of their area.

Other features which are considered as characteristic for the invention are set forth in the appended claims.

Although the invention is illustrated and described herein as embodied in a method for monitoring a structure by measuring electrical quantities, an apparatus and a measuring head for carrying out the method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 3 is a fragmentary, side-elevational view of the measuring head with a holder;

FIG. 4 is a fragmentary perspective view of a basic measuring setup for illustrating the physical fundamentals of the measurement; and FIG. 5a is another fragmentary, elevational view showing the basic construction of the measuring head showing the first loop including a cross-hatched area close to the surface of the component.

FIG. 5b is a fragmentary view similar to FIG. 5a showing the second loop as a cross-hatched area above the first loop.

Figure 1:
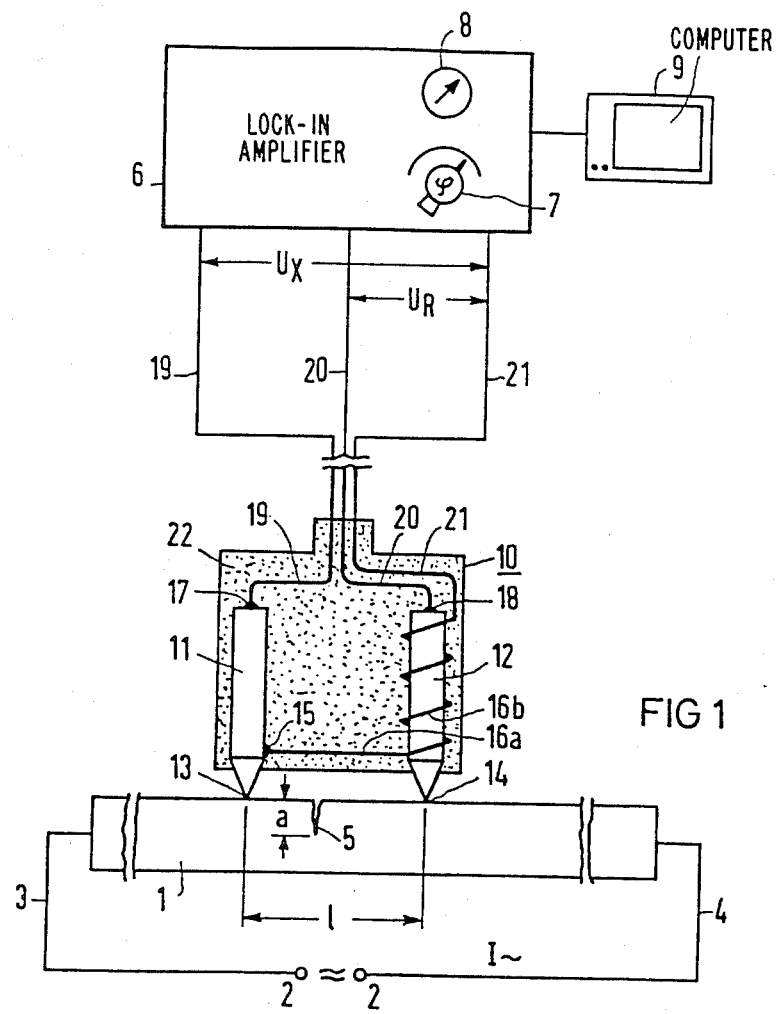
FIG. 1 is a fragmentary, diagrammatic, front-elevational view of a measuring head according to the invention with a measuring apparatus.

Referring now to the figures of the drawings in detail and first, particularly, to FIG. 1 thereof, there is seen an electrically conducting component 1 which is connected by means of leads 3, 4 to an a-c source 2, so that an a-c current I~ can flow through it. For reasons of measuring accuracy, the direction of the current flow should be chosen in the load direction of the component. It is possible for material faults to be present in the component, such as small cracks 5 which are to be detected. The depth a of the cracks is of particular interest. For this purpose, a measuring head is placed on the structure 1 to be examined. The measuring probe includes two electrically conducting pins 11, 12 which are provided with points 13, 14 at the lower ends thereof. The current carrying component 1 produces a certain voltage drop per unit length, corresponding to the current. The measuring points 13, 14 spaced apart by a spacing l tap this voltage across the area to be examined. The more cracks 5 or other faults the component 1 contains, the larger is the tapped voltage. However, the voltage to be measured is very small and can only be measured with a special measuring device because of various disturbances and the ever-present noise. The measuring device is formed of suitable electronic measuring circuitry 6, preferably including a phase-selective amplifier or a so-called lock-in amplifier. This amplifier selectively amplifies only the signals which arrive with the measuring frequency and a certain phase relative to this measuring frequency. The voltage tapped-off at the points 13, 14 is fed to such a lock-in amplifier 6. The area between the two leads in this case is as small as possible. For this purpose, the measuring pin 11 has a tap 15 at this lower end, as close as possible to the point 13, from which a first electrically insulated line 16a is conducted to a location on the other pin 12 which is above and as close as possible to the surface of the component 1. The electrical line is then conducted upward in a helical section 16b around this pin 12. A second lead which is conducted to the lock-in amplifier 6 starts at a tap 18 at the upper end of the measuring pin 12, from which a lead 20 is conducted to the lock-in amplifier 6. The line 16b also continues to the lock-in amplifier 6 in the form of a lead 21. A lead 19 is also conducted from a tap 17 at the upper end of the measuring pin 11 to the lock-in amplifier 6. Contrary to the embodiment illustrated in FIG. 1, the lines 20, 21 with the line 19 may optionally be heavily twisted together in order to reduce influences caused by electromagnetic stray fields. The lines 20, 21 form the measuring input of the lock-in amplifier for measuring a voltage $U_R$ between the measuring points 13, 14.

The lock-in amplifier furthermore requires information regarding the phase $\phi$, by means of which the measuring voltage is to be selected with respect to the a-c voltage source 2. In principle, this information could be fed to the lock-in amplifier 6 from the a-c voltage source 2, but it has been found that the current in the component 1 may be phase-shifted relative to the current source 2, especially after the leads 3, 4 are installed. According to the invention, the information regarding the phase of the a-c current is therefore likewise obtained directly at the measuring point. To this end, the measuring head 10 has a conductor loop in the interior thereof which is formed by the measuring pin 11, the line 16a, the helical line section 16b and the line 19. A voltage $U_X$ which can be utilized as the reference signal for the phase information is induced in this conductor loop, corresponding to the change of the magnetic flux $\emptyset$. The voltage $U_X$ is fed to the lock-in amplifier by means of the line 21 and the line 19 starting at the tap 17. The voltage $U_R$ to be measured must always have a phase shift of 90° relative to the voltage $U_X$. This may be set at the lock-in amplifier 6 by means of a phase control 7. The value of the voltage $U_R$ which is now frequency-selectively measured with the phase of 90°, can be indicated on a measuring instrument 8 or can be fed to a computer 9 for further processing and evaluation. The computer can optionally carry out the automatic readjustment of the phase $\phi$ in conjunction with the lock-in amplifier, if the operating conditions have changed. However, the voltage $U_X$ can be measured with a corresponding phase shift relative to the voltage $U_R$, so that the local resistance at the measuring point can be determined.

The measuring head itself should be constructed as a stable unit; for instance, it can be cast in a block 22 of suitable material. This material should be temperature-resistant but should also be elastic with respect to thermal expansion. For instance, water glass is a suitable material.

Figure 2:
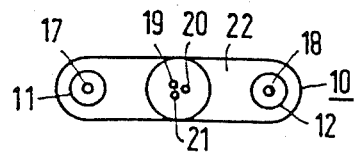
FIG. 2 is a top-plan view of a measuring head.

FIG. 2 is a top view of the measuring head. Cast into the block 22 are the pins 11, 12 with the leads and the counter loop. The three lines 19, 20, 21 protruding from the head, are preferably heavily twisted with each other. As described above, such a measuring head can be used as a mobile probe, so that different areas of a structure can be examined sequentially.

FIG. 3 illustrates a special mounting for a measuring probe according to the invention, which makes it possible to repeatedly place it onto the structure or component with a defined pressure. To this end, the probe 10 is disposed in a holding frame 30 to which it is braced by means of compression springs or other elastic elements 32. The frame has legs 31, against which the component 1 can be pressed. These legs 31 can also be equipped with magnets or holding bands or the like for fastening to a structure. The holding frame 30 should preferably be formed of electrically non-conductive material, so that the measurement is not influenced.

Instead of a mobile probe, fixed measuring heads can, of course, also be used, and pins that are welded-on or otherwise durably fastened to the structure can be used instead of the measuring pins 13, 14. The measuring principle remains unaffected by using these alternatives. It is also especially advantageous to use an identical reference probe at an undamaged or unstressed point of the structure so that a difference measurement can be made instead of an absolute measurement. This increases the validity of the measurement.

The physical relationship during the measurement are explained once more with reference to FIGS. 4 and 5. The component 1 carries an a-c current I flowing in the direction of the arrow. This produces a magnetic alternating field $\emptyset$ perpendicular to the direction of the current. According to Maxwell's equations, the magnetic flux in the vicinity of a definite point of the component to be examined is proportional to the current flowing at that point. The alternating magnetic field induces a voltage in a conductor loop which is phase-shifted 90°. Therefore, the a-c current flowing at a given point of the structure can be measured by means of the alternating magnetic field generated thereby. For this purpose, a conductor loop is needed, in which a voltage $U_X$ is generated that is proportional to the alternating magnetic field but is phase-shifted 90°. The voltage $U_X$ therefore contains the information regarding the magnitude of the current at the point in question in the component 1. If the voltage $U_R$ is simultaneously tapped at the point of the component 1 over a given length, the resistance per unit length can be calculated from these two items of information, i.e., a kind of "resistivity" of the structure at the given measuring frequency is calculated. The resistance at the point of measurement allows conclusions to be drawn regarding the damage in this region and possibly also regarding the depth of the cracks, as will be explained below, referring to several examples.

In FIG. 5, the measuring head is again shown diagrammatically, with the area of the conductor loop being sectioned. This area which is bounded by the pin 11 and the lines 16a, 16b and 19 determines the magnitude of the voltage $U_X$. The area should be chosen in such a way that the voltages $U_X$ and $U_R$ are of the same order of magnitude, so that errors at the lock-in amplifier due to measuring range switching do not occur. Optionally, the conductor loop could also be formed of two or more turns of smaller area, if, for instance, this is required by the overall height of the probe. This would not change the principle of the measurement. It also does not matter at which point of the probe the measuring lines 19, 20, 21 are brought to the outside as long as they are heavily twisted with each other in order to eliminate interference. In general, the use of heavily twisted lines is recommended, particularly for the leads from the a-c current source to the component 1, to the extent that this is possible.

As is indicated in FIG. 5, a certain increased resistance at a measuring point can be explained by one large crack 5 or by several small damages 50. At this location an equivalent crack depth will be generally determined from the measured resistance in accordance with prior reference measurements, in which case the worst state of the component which could have this resistance is assumed by conservative assumptions.

The invention is based on the following theoretical formulations:

The measurement is performed at a suitable permanently preselected frequency F which is chosen in dependence on the material and the desired depth of penetration.

The desired information regarding the state of the material is obtained from the "resistivity" $\rho'$ at the point to be examined. The "resistivity" $\rho$ of the undamaged material at the measuring frequency F is known or can be determined by a reference measurement. If the material contains cracks or other damage at the measuring point to be examined, the resistivity $\rho'$ is increased, but does not allow direct conclusions to be drawn as to the type of damage. By changing the measuring frequency F, the depth of the current path $\sigma$, i.e., the depth of penetration of the a-c current I~ into the structure can be changed according to the relationship $$\sigma = \frac{\rho}{\mu_r \cdot \mu_o \cdot F \cdot \pi},$$

where $\mu_r$ is the relative permeability of the material and $\mu_o$ is a permeability constant, from which further information regarding the type of damage can be obtained.

With a constant a-c current I~, the measurement of the change of the resistivity $\rho'$ can be reduced in a first approximation to a voltage measurement $U_R$ over two measuring points at a distance l. However, an unchangeable current density distribution in the structure must be assumed, which is not always the case. It is better to measure the voltage $U_R$ as well as the current $I_{meas}$ flowing at the measurement point in order to determine the following relationship according to Ohm's law:

$$\rho' = \frac{U_R \cdot l}{I_{meas}}.$$

$I_{meas}$ is determined by a conductor loop located near the measuring point, in which the change $d\phi$ of the magnetic flux $\phi$ generated by the current $I_{meas}$ induces a voltage $U_X$.

The magnitude of the voltage $U_X$ also depends on the area and, if applicable, the number of turns of the conductor loop, which is taken into consideration by a probe constant $C_{Sonde}$ (if the surface of the conductor loop is not disposed parallel to the connecting line of the measurement points for $U_R$ and/or is not perpendicular to the surface of the structure, further geometrical factors must be taken into consideration). The relationship $$\rho' = \frac{U_R}{U_X} \cdot C_{Sonde}$$

is therefore developed, where $C_{Sonde}$ is determined by reference measurements, for instance. Since $U_X$ is phase-shifted 90° relative to $U_R$, this must be taken into consideration in forming the ratio, which is possible with great accuracy in a lock-in amplifier, for instance.

The value $U_R$ determined in this manner is largely measurable free of interference and is well suited for characterizing the condition of the material.

The evaluation of the measurement becomes particularly simple if $U_R$ and $U_X$ are measured as complex voltages with a real and an imaginary part in any desired reference system, namely:

$$\overline{U_R} = \text{real part } (\overline{U_R}) + \text{i.imaginary part } (\overline{U_R})$$

$$\overline{U_X} = \text{real part } (\overline{U_X}) + \text{i.imaginary part } (\overline{U_X}).$$

The presentations of $U_R$ and $U_X$ in polar coordinates in the reference system can be obtained therefrom by a recalculation, namely:

$$\overline{U_R} = (|U_R| \cdot \phi_R) \text{ and } \overline{U_X} = (|U_X| \cdot \phi_X).$$

The complex "resistivity" $\rho'$ at the point of measurement is obtained from $$\overline{\rho'} = U_R/U_X \cdot e^{i(\phi_R - \phi_X + 90°)},$$

where the real part of $\overline{\rho'}$ is obtained as $$\text{real part } \overline{\rho'} = |\rho'| \cdot \cos(\phi_R - \phi_X + 90°).$$

A direct statement regarding the condition of the material and the depth of possible cracks can be obtained from this value, optionally in comparison with a reference point of measurement.

The probe according to the invention is also suitable for other measurements beyond the expressly described application. Thus, for instance, the wall thickness of tubes can be monitored with the method, or material parameters such as temperature and the like can be determined; under some circumstances this can also be done with melts or liquids.

We claim:

1. Method for monitoring structures by measuring electrical quantities, which comprises subjecting an electrically conducting component to an ac current with a predetermined frequency in a given direction generating a magnetic flux in a given direction, measuring a voltage drop across two measurement points mutually spaced apart by a given distance at individual partial regions of the component by means of two measuring lines contacting the component, a segment of one of said measuring lines extending parallel to said component, in closely spaced relation thereto, from the region of one of said measurement points to the region of the other one of said measurement points, wherein said two measuring lines, including said segment of said one of said measuring lines extending between said two measurement points, and the component disposed between said two measurement points form a first conductor loop with an inductively effective area between said segment and said component being as small as possible mesuring an induction voltage from the change of the magnetic flux as close as possible to said two measuring points by means of a second conductor loop being substantially parallel to the given direction of the current and perpendicular to the given direction of the magnetic flux; feeding the voltage drop and the induction voltage to an electronic evaluation circuit, and deriving the local resistance of the component at the measurement points from the voltage drop and the induction voltage with the evaluation circuit.

2. Method according to claim 1, which comprises preamplifying the voltage drop and the induction voltage before feeding them to the evaluation circuit.

3. Method according to claim 1, which comprises considering the phase relationships of the voltage drop and the induction voltage relative to each other when deriving the local resistance with the evaluation circuit.

4. Method according to claim 1, which comprises considering the phase relationships of the voltage drop and the induction voltage relative to the a-c current when deriving the local resistance with the evaluation circuit.

5. Method according to claim 1, which comprises deriving quantities significant for determining the condition of the component with the evaluation circuit, besides deriving the local resistance.

6. Method according to claim 1, which comprises sequentially measuring the electrical quantities under the same conditions with identical measuring apparatus at a region to be examined at an unstressed and undamaged reference measuring point.

7. Method according to claim 1, which comprises simultaneously measuring the electrical quantities under the same conditions with identical measuring apparatus at a region to be examined at an unstressed and undamaged reference measuring point.

8. Method according to claim 1, which comprises measuring and keeping constant the phase relationships between the a-c current and the measured voltage drop and induction voltage with a frequency and phase selective lock-in amplifier in the evaluation circuit.

9. Method according to claim 8, which comprises automatically readjusting the phase at the lock-in amplifier with each measurement for measuring the prevailing voltage drop with a phase shift that is always exactly 90° relative to the corresponding induction voltage.

10. Method according to claim 9, which comprises accurately measuring the induction voltage and forming a ratio of the induction voltage to the phase-shifted voltage drop as a measure of damage to and change in the component.

11. Apparatus for monitoring structures by measuring electrical quantities, comprising a measuring device including an a-c current source connected to a component for subjecting the component to an a-c current in a given direction generating a magnetic flux in a given direction, two measuring lines contacting respective measurement points on the surface of the component for measuring a voltage drop, a segment of one of said measuring lines extending parallel to said component, in closely spaced relation thereto, from the region of one of said measurement points to the region of the other one of said measurement points, an electronic evaluation circuit connected to said measuring lines, said measuring lines, including said segment of said one of said measuring lines extending between said two measurement points, said electronic evaluation circuit and the component together forming a first conductor loop with an inductively effective area between said segment and said components being as small as possible, further comprising a second conductor loop having a predetermined area, being substantially parallel to the given direction of the a-c current and perpendicular to the given direction of the magnetic flux for measuring the change of the magnetic flux as an induction voltage, said predetermined area being formed by measuring lines and being as close as possible to the measurement points and to the surface of the component, and an electronic evaluation circuit connected to said measuring lines being part of said second conductor loop for measuring said induction voltage.

12. Apparatus according to claim 11, wherein said evaluation circuit includes means for measuring said induction voltage while considering the phase relationship of said voltage drop and said induction voltage relative to each other.

13. Apparatus according to claim 11, wherein said evaluation circuit includes means for measuring said induction voltage while considering the phase relationship of said voltage drop and said induction voltage relative to said a-c current.

14. Apparatus according to claim 11, wherein said measuring device is attached to a location of the component with known properties, and including at least one other measuring device identical to said first-mentioned measuring device being attached to at least one location of the component to be examined.

15. Apparatus according to claim 11, including a measuring head having first and second pins electrically conductingly contacting the measurement points of the component, said first and second pins having upper ends and said second pin having a tap, said measuring lines being in the form of a first measuring line connected to said upper end of said first pin and a second measuring line having an upper region twisted with said first measuring line up to said upper end of said first pin and another region ending at said tap of said second pin, and including a lead fastened to said upper end of said second pin and twisted with said measuring lines, said measuring head additionally including said second conductor loop including said second pin, said lead twisted with said measuring lines and said second measuring line.

16. Apparatus according to claim 15, wherein said other region of said second measuring line is wound around said first pin.

17. Apparatus according to claim 15, wherein said other region of said second measuring line is adjacent said first pin.

18. Apparatus according to claim 15, wherein said other region of said second measuring line is adjacent the surface of the component.

19. Apparatus according to claim 15, wherein said measuring head is a compact unit cast over with electrically insulating material.

20. Apparatus according to claim 15, wherein said measuring head is a compact unit cast over with water glass.

21. Apparatus according to claim 15, wherein said measuring head is a mobile probe and said pins have hardened points at lower ends thereof to be pressed against the component.

22. Apparatus according to claim 21, including a holding frame for said measuring head having support elements defining a contact surface for the component and means for biasing the top of said measuring head against the component, said pins protruding beyond said contact surface in a relaxed condition of said biasing means.

23. Apparatus according to claim 15, wherein said measuring head, said measuring lines and said lead twisted thereto form a prefabricated unit disposed on and connected to said pins with electrical contact.

24. Apparatus according to claim 15, including a preamplifier integrated in said measuring head.

* * * * *